United States Patent [19]

Paulson et al.

[11] Patent Number: 5,047,335
[45] Date of Patent: Sep. 10, 1991

[54] PROCESS FOR CONTROLLING INTRACELLULAR GLYCOSYLATION OF PROTEINS

[75] Inventors: James Paulson, Sherman Oaks; Eryn Ujita-Lee, Redondo Beach; Jasminder Weinstein, Culver City, all of Calif.

[73] Assignee: The Regents of the University of Calif., Berkeley, Calif.

[21] Appl. No.: 288,618

[22] Filed: Dec. 21, 1988

[51] Int. Cl.$^5$ .................. C12N 15/00; C12N 15/56; C12N 15/79
[52] U.S. Cl. .................. 435/69.1; 435/320.1; 435/172.3; 435/240.1; 435/254; 935/50; 935/60; 536/27
[58] Field of Search .................. 435/69.1, 320, 172.3; 536/27; 935/60, 50

[56] References Cited

U.S. PATENT DOCUMENTS

| | | | |
|---|---|---|---|
| 4,656,134 | 4/1987 | Ringold | 435/91 |
| 4,695,542 | 9/1987 | Yokota et al. | 435/172.3 X |
| 4,740,461 | 4/1988 | Kaufman | 435/172.3 |
| 4,743,679 | 5/1988 | Cohen et al. | 530/350 |
| 4,758,511 | 7/1988 | Martens et al. | 435/172.3 X |
| 4,770,999 | 9/1988 | Kaufman et al. | 435/172.3 X |
| 4,775,624 | 10/1988 | Bang et al. | 435/226 |

OTHER PUBLICATIONS

Narimatsu et al, 1986, Proc. Natl. Acad. Sci. U.S.A., vol. 83, pp. 4720–4724.
Kadam et al, 1985, Journal of Bacteriology, vol. 161, pp. 277–284.
J. Weinstein, et al., Primary Structure of β-Galactoside α2,6-Sialyltransferase, Journal of Biological Chemistry, pp. 17735–17743, Dec. 25, 1987.
J. Weinstein, et al., Sialylation of Glycoprotein Oligosaccharides N-Linked to Asparagine, Journal of Biological Chemistry, Nov. 25, 1982, pp. 13845–13853.
M. Takeuchi et al., Comparative Study of the Asparagine-Linked Sugar Chains of Human Erythropoietins Purified From Urine and the Culture Medium of Recombinant Chinese Hamster Ovary Cells, Jour. of Bio. Chem., Mar. 15, 1988, pp. 3657–3663.

*Primary Examiner*—Richard A. Schwartz
*Assistant Examiner*—S. L. Nolan
*Attorney, Agent, or Firm*—Poms, Smith, Lande & Rose

[57] ABSTRACT

A process for controlling the glycosylation of protein in a cell wherein the cell is genetically engineered to produce one or more enzymes which provide internal control of the cell's glycosylation mechanism. A Chinese hamster ovary (CHO) cell line is genetically engineered to produce a sialyltransferase. This supplemental sialyltransferase modifies the CHO glycosylation machinery to produce glycoproteins having carbohydrate structures which more closely resemble naturally occurring human glycoproteins.

16 Claims, 3 Drawing Sheets

Fig. 3a

```
-182                                                                                                                            CG  -181
-180  GTT TTT GAT CAT CCT GAG AAA AAT GAG CCT TGG CCT CCA GAC CTA GTG AAG TAA CCT CTT TCT CAT GGA GAA CAG TGC TGG CTC CTG AGG   -91
- 90  ATC TGG AGG GCC TGC AGC CCC AGA GGG ATT AGC CAG AAG CAG GCG TGG TTC CTG CTC TGC ACA GTG GCT CTC CTG TCT GGA CCA TTC ATT   - 1
  1   ATG ATT CAT ACC AAC TTG AAG AAA AAG TTC AGC CTC TTC GCA GTC ATC TGT GTT AAG AAA GGG AGC       90
  1   MET Ile His Thr Asn Leu Lys Lys Lys Phe Ser Leu Phe Ala Val Ile Cys Val Trp Lys Lys Gly Ser   30
 91   GAC TAT GAG GCC CTT ACA CTG CAA GCC AAG GAA TTC CAG ATG CCC AAG AGC CAG GTG TCT GCT TCC CAG GTT GTG   180
 31   Asp Tyr Glu Ala Leu Thr Leu Gln Ala Lys Glu Phe Gln Met Pro Lys Ser Gln Val Ala Met Gly Ser Ala Ser Gln Val Val   60
181   TTC TCA AAC AGC CAA GAC CCT AAG GAA GAC ATT CCA ATC CTC AGT TAC TAC CAC AGG GTC ACA CAG CCT TCC TTC   270
 61   Phe Ser Asn Ser Gln Asp Pro Lys Glu Asp Ile Pro Ile Leu Ser Tyr His Arg Val Thr Ala Lys Val Pro Gln Pro Ser Phe   90
271   CAG GTG TGG GAC AAG GAC TCC ACA TAC.TCA AAA CTT AAC CCC AGG CTG CTG AAG ATC TGG AGA AAC ATG AAC AAA TAT CTG AAC ATG AAC AAA TAT AAA   360
 91   Gln Val Trp Asp Lys Asp Ser Thr Tyr Ser Lys Leu Asn Pro Arg Leu Leu Lys Ile Trp Arg Asn Met Asn Lys Tyr Lys   120
361   GTA TCC TAC AAG GGA CCG GGG CCA GGA GTC AAG TTC AGC GTA GAA GCA CTG CGT TGC CAC CTT CGA GAC CAT GTG AAC GTG TCT ATG ATA   450
121   Val Ser Tyr Lys Gly Pro Gly Pro Gly Val Lys Phe Ser Val Glu Ala Leu Arg Cys His Leu Arg Asp His Val Asn Val Ser Met Ile   150
451   GAG GCC ACA GAT TTT CCC TTC AAC ACC ACT GAG TGG GAG GGT TAC CTG CCC AAG GAG AAC TTT AGA GAG TTT GGG CCT TGG CAA AGG   540
151   Glu Ala Thr Asp Phe Pro Phe Asn Thr Thr Glu Trp Glu Gly Tyr Leu Pro Lys Glu Asn Phe Arg Thr Lys Val Gly Pro Trp Gln Arg   180
541   TGT GCC GTC GTC TCT GCA GGA TCT CTG AAA AAC TCC CAG GTT GGT CGA GAG ATT GAT AAT CAT GAT GCA GTT CTG AGG TTT AAT GGG   630
181   Cys Ala Val Val Ser Ser Ala Gly Ser Leu Lys Asn Ser Gln Leu Gly Arg Glu Ile Asp Asn His Asp Ala Val Leu Arg Phe Asn Gly   210
```

Fig. 3.b

```
631  GCC CCT ACC GAC AAC TTC CAA CAG GAT GTG GGC TCA AAA ACT ACC ATT CGC CTA ATG AAC TCT CAG TTA GTC ACC GAA AAG CGC TTC  720
211  Ala Pro Thr Asp Asn Phe Gln Gln Asp Val Gly Ser Lys Thr Thr Ile Arg Leu Met Asn Ser Gln Leu Val Thr Glu Lys Arg Phe  240

721  CTC AAG GAC AGT TTG TAC ACC GAA GGA ATC CTA ATT GTA GAC CCA TCC GTG TAT CAT GCA GAT ATC CCA AAG TGG TAT CAG AAA CCA  810
241  Leu Lys Asp Ser Leu Tyr Thr Glu Gly Ile Leu Ile Val Asp Pro Ser Val Tyr His Ala Asp Ile Pro Lys Trp Tyr Gln Lys Pro  270

811  GAC TAC AAT TTC TTC GAA ACC TAT AAG AGT TAC CGA AGG CTG AAC CCC AGC CAG CCA TTT TAT ATC CTC AAG CCC CAG ATG CCA TGG GAA  900
271  Asp Tyr Asn Phe Phe Glu Thr Tyr Lys Ser Tyr Arg Arg Leu Asn Pro Ser Gln Pro Phe Tyr Ile Leu Lys Pro Gln Met Pro Trp Glu  300

901  CTG TGG GAC ATC ATT CAG GAA ATC TCT GCA GAT CTG ATT CAG CCA AAT CCC CAG CCA ATG TCC GGT ATC ATG CTG GGT ATC ATC ATC ATG ACG  990
301  Leu Trp Asp Ile Ile Gln Glu Ile Ser Ala Asp Leu Ile Gln Pro Asn Pro Ser Pro Met Ser Gly Ile Met Leu Gly Ile Ile Ile Met Thr  330

991  CTG TGT GAC CAG GTA GAT ATT TAC GAC CCG CTC TTC GAG TTC CTC CTC TTC GAG AAG ACG GAC GTG TGC TAT TAT CAC CAA AAG TTC TTT GAC AGC GCT  1080
331  Leu Cys Asp Gln Val Asp Ile Tyr His Pro Leu Phe Glu Phe Leu Leu Phe Glu Lys Thr Asp Val Cys Tyr Tyr His Gln Lys Phe Phe Asp Ser Ala  360

1081 TGC ACG ATG GGT GCC TAC GAC CTT TCT ACC CTT GGC TTC GAG AAG CAT CTC AAT ATG GTG AAG AAA CAT GAA GGA ACA GAT GAA GAT ATT TAT TTG TTT  1170
361  Cys Thr Met Gly Ala Tyr Asp Leu Ser Thr Leu Gly Phe Glu Lys His Leu Asn Met Val Lys Lys His Glu Gly Thr Asp Glu Asp Ile Tyr Leu Phe  390

1171 GGG AAA GCC ACC ACC CTT TCT TGC TTC CGG AAC ATT CGT TGT TGA CCT AGC CAG GCA CCC TTA TCC TTC TCC ATA CGT CAT TTT ATG GCT  1260
391  Gly Lys Ala Thr Thr Leu Ser Cys Phe Arg Asn Ile Arg Cys *** .........                                                      403

1261 ACT CTC CTG GTT ACC GCT CTG TGA AGG AGT GTT ATT CAA CAG GCC CAG CCT GCT TCC TGC GCT CTA GGG AAT TTT GTT GGC AAG AGT  1350

1351 TCT GGC GCC TCC AGC CTG CCT CCC TGG GGC CAC CGA GGA TGG CAC GTC GAG TCC AGA TTC TTG CCA CAC TCA TTC CTC CTA GAC GTC AGC AGC GTC CTC TCC  1440

1441 TCC TTC TGC ATG AGG GGT GAA AG                                                                                              1463
```

PROCESS FOR CONTROLLING INTRACELLULAR GLYCOSYLATION OF PROTEINS

This invention was made with Government support under Grant No. GM-27904 awarded by the National Institutes of Health. The Government has certain rights in this invention.

BACKGROUND OF THE INVENTION

1. Field of the Invention.

The present invention relates generally to the cellular mechanisms and machinery involved in the glycosylation of proteins manufactured by the cell. More particularly, the present invention involves altering the glycosylation capabilities of a cell in order to control the structure of carbohydrate groups attached during glycosylation.

2. Description of Related Art.

The publications and other reference materials referred to herein to describe the background of the invention and to provide additional detail regarding its practice are hereby incorporated by reference. For convenience, the reference materials are numerically referenced and grouped in the appended bibliography.

During the last decade, numerous processes and procedures have been developed for genetically engineering cells in order to produce a wide variety of proteins and glycoproteins. These procedures involve utilizing recombinant DNA technology to prepare a vector which includes genetic material that codes for a specific protein or glycoprotein. Upon introduction of the vector into the host cell, the inserted genetic material instructs the host cell's biochemical machinery to manufacture a specific protein or glycoprotein.

Problems have been experienced with the production of glycoproteins by genetically engineering host cells. Glycoproteins are proteins having carbohydrate groups attached at various points along the protein's amino acid backbone. The carbohydrate groups are commonly attached to asparagine, serine or threonine. The genetic sequence introduced into the host cell usually includes instructions with respect to the amino acid sequence of the protein and the location and structure of the carbohydrate groups. Most of the cell lines which are commonly used as host cells are capable of following the vector's instructions with respect to preparing a protein having a specific amino acid sequence. However, many host cells are not capable of following instructions with respect to glycosylation of the protein. For example, *E. coli* is a common host cell used in producing a wide variety of proteins. However, *E. coli* does not contain the cellular glycosylation machinery required to attach carbohydrate groups to the proteins it manufactures.

Unlike *E. coli*, many other host cells do have varying capabilities with respect to protein glycosylation. However, even though these cells have glycosylation capabilities, the glycosylation machinery is not controlled by the recombinant DNA vector. Accordingly, the glycoprotein produced by such host cells may differ in carbohydrate structure from the natural glycoprotein coded for by the vector.(1, 2)

Chinese hamster ovary (CHO) cells are a standard cell line used commercially for the high yield expression of glycoproteins from vectors engineered through recombinant DNA technology. The protein sequence of the glycoprotein expressed by CHO comes from the DNA transinfected into the cell while the structure of the carbohydrate portion of the glycoprotein is determined by the cellular machinery of the CHO cells. While most glycoproteins normally contain a mixture of NeuAc-α-2,6Gal and NeuAc-α-2,3Gal linkages on their N-linked oligosaccharides, CHO cells only make asparagine linked carbohydrate chains with terminal sialic acids in the NeuAc-α-2,3Gal linkage.(1,2)

For example, erythropoietin is a glycoprotein naturally occurring in humans which has N-linked carbohydrate groups with both the NeuAc-α-2,6Gal and NeuAc-α-2,3Gal linkages. CHO cells which are genetically engineered to produce erythropoietin can only produce this protein with the NeuAc-α-2,3Gal linkages.(1) Although a number of mutant CHO cell lines have been developed which have altered capabilities for protein glycosylation,(3) they are not suitable for the production of glycoproteins intended for use in animals. Indeed, the carbohydrate groups produced by the cells are truncated, resulting in the rapid clearance of the recombinant glycoproteins from the blood followed by degradation. Thus, while the glycoproteins produced by these mutant CHO cell lines do display in vitro biological activity, they are inactive in vivo because of the rapid clearance from the blood stream.

From the above, it is apparent that there is a need to develop a process which can be used to alter the glycosylation machinery of host cells in order to control the structure of carbohydrates attached during glycosylation. Such a process for controlling host cell glycosylation would be useful not only in expressing glycoproteins which accurately mimic naturally occurring proteins, but would also be useful in preparing glycoproteins having selected altered carbohydrate structures for diagnostic and research uses.

SUMMARY OF THE INVENTION

In accordance with the present invention, a process is disclosed which provides for control of cellular glycosylation. The invention is based upon the discovery that the glycosylation machinery of host cells can be altered and controlled by introducing a gene into the host cell which codes for at least one enzyme which is capable of affecting glycosylation of a protein in the cell.

The present invention involves controlling the glycosylation of a protein in a host cell wherein attachment of the carbohydrate moiety to proteins during glycosylation is dependent upon a number of naturally occurring enzymes which are present in the cell. In accordance with the present invention, at least one gene is introduced into the cell which is capable of expressing at least one supplemental enzyme which is capable of affecting the glycosylation mechanism. The expression of the supplemental enzyme in the cell produces a cell having both naturally occurring and supplemental enzymes wherein the presence of the supplemental enzyme alters the cell's glycosylation mechanism.

As a feature of the present invention, it was discovered that transfection of CHO cells with cDNA coding for a glycosyltransferase resulted in production of the glycosyltransferase enzyme in the CHO cell and subsequent alteration of the carbohydrate structure of glycoproteins produced by the CHO cell.

A feature of the present invention is that the glycosylation machinery of a host cell can be controlled to produce glycoproteins wherein the location and structure of carbohydrates is equivalent to a given naturally occurring glycoprotein. As an additional feature of the present invention, the glycosylation process of the host cell can also be controlled to produce glycoproteins wherein the carbohydrate structure is changed slightly from the naturally occurring glycoprotein. Such purposely altered glycoproteins are useful as both diagnostic and research tools in studying the biochemistry of various naturally occurring glycoproteins.

The above discussed and many other features and attendant advantages of the present invention will become better understood by reference to the following detailed description when taken in conjunction with the accompanying drawings.

BRIEF DESCRIPTION OF THE DRAWINGS

FIGS. 3a and 3b are the nucleotide sequence of the sialtransferase cDNA prior to mutagenisis at the EcoRI site.

DETAILED DESCRIPTION OF THE INVENTION

Figure 1:
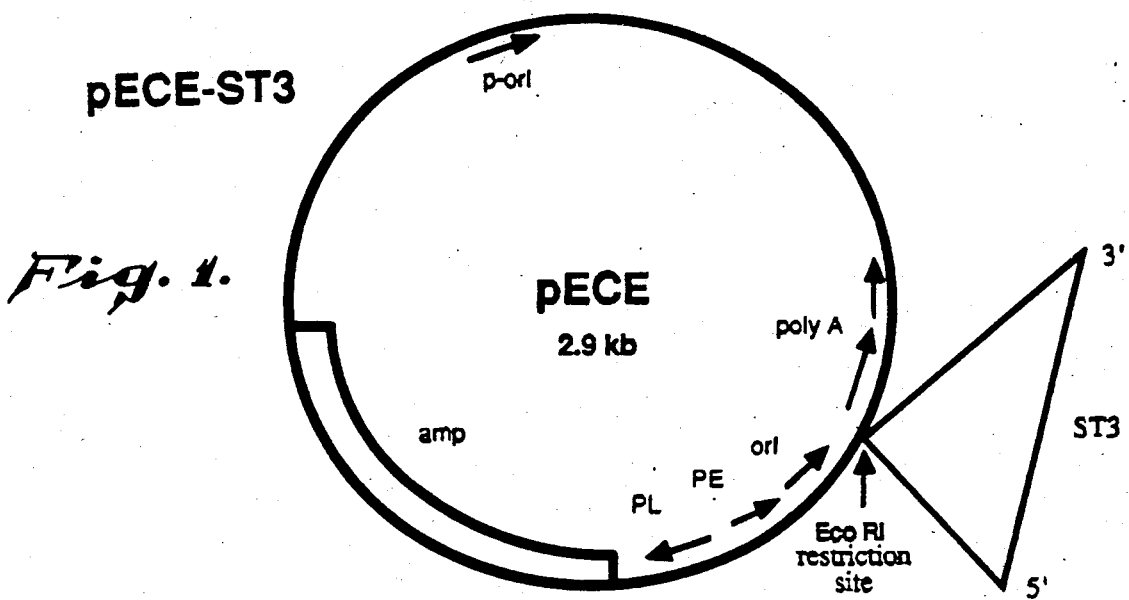
FIG. 1 is a diagram showing the plasmid construct used to transfect CHO cells to alter the terminal structures of the N-linked carbohydrate groups by expression of sialyltransferase. The vector was constructed by inserting a cDNA coding for the sialyltransferase into the cloning site of the pECE expression vector described by Ellis, et al.(4)

The present invention involves controlling the glycosylation machinery of a cell by using genetic engineering to instruct the cell to produce various enzymes upon which glycosylation in the cell is dependent. The process for controlling glycosylation is based on the well-documented fact that a given cell will synthesize carbohydrate groups whose structures are determined by the specificities of the glycosyltransferases produced by that cell. (2) The most bioactive terminal sugars are attached to common core structures by "terminal" glycosyltransferases.(5) When two terminal enzymes compete with each other, the ultimate carbohydrate structure is determined by the specificity of the enzyme that acts first. The invention relies on the concept that the introduction and over expression of a terminal (or branching) glycosyltransferase, not normally produced by a cell, will result in the successful competition with the endogenous enzymes, and will produce carbohydrate groups with a structure specified by the new enzyme.

The basic procedure involves transfection of a host cell with a vector carrying a gene which expresses at least one enzyme upon which glycosylation in the host is dependent. The resultant enzyme(s) which is expressed in the cell provides internal control of the glycosylation machinery of the cell. Accordingly, the invention provides a useful procedure for controlling the structure of carbohydrates attached during glycosylation to more closely resemble naturally occurring glycolipids. In addition, one can use the present invention to alter the carbohydrate structure of a glycoprotein produced in a host cell for investigational purposes.

The invention has wide application to host cells which are naturally capable of glycosylation. Exemplary cell lines to which the present invention is amenable include Chinese hamster ovary (CHO) cells, mouse L cells, mouse A9 cells, baby hamster kidney cells, C127 cells, PC8 cells and other eukaryotic cell lines capable of the expression of recombinant glycoproteins.

The particular procedure used to introduce genetic material into the host cell for expression of the glycosyl transferase is not particularly critical. Any of the well-known procedures for introducing foreign nucleotide sequences into host cells may be used. These include the use of plasmid vectors, viral vectors and any of the other well-known methods for introducing cDNA or other foreign genetic material into a host cell. It is only necessary that the particular genetic engineering procedure utilized be capable of successfully introducing at least one gene into the host cell which is capable of expressing at least one enzyme which is known to be involved in glycosylation. Further, the genetic material must be introduced in such a way that the host cell expresses the enzyme coded for by the inserted genetic material so that, upon expression, the enzyme alters the glycosylation capabilities of the cell.

The preferred enzymes for production within a host cell are glycosyltransferases such as sialyltransferase. Other possible enzymes which may be coded for and produced within the cell to alter the glycosylation machinery include fucosyltransferases, galactosyltransferases, $\beta$-acetylgalactosaminyltransferases, N-acetylglycosaminyltransferases, and sulfotransferases.(5)

The particular vector used is also not particularly critical. Any of the conventional vectors used for expression of recombinant glycoproteins in eukaryotic cells may be used. Exemplary vectors include pMSG, pAV009/A+, pMT010/A+ and any other vector allowing expression of glycoproteins under direction of the SV-40 early promotor, metallothionein promotor, murine mammary tumor virus promotor, Rous sarcoma virus promotor or other promotors shown effective for expression in eukaryotic cells. A suitable vector is the pECE vector which is described in Ellis, et al.(4)

The types of glycoprotein which would be expressed having modified carbohydrate structural forms include erythropoietin, insulin, plasminogen activator (TPA), interferon and various glycopeptide hormones. The nucleotide sequences for various cDNA coding for these proteins are known.

The following portion of this detailed description is limited to alteration of the glycosylation machinery of CHO cells. However, it is understood that the principles disclosed with respect to the CHO cell line also apply to the other various host cells previously mentioned.

In this specific example, a CHO cell line is produced which produces modified terminal sialic acid groupings on its N-linked oligosaccharides. Normally these cells make N-linked carbohydrate groups that contain sialic acid exclusively in the NeuAc$\alpha$ 2,3Gal sequence. By expression of a $\beta$-galactosideo$\alpha$ 2,6 sialyltransferase cDNA in these cells, the N-linked carbohydrate groups are directed to produce the NeuAc$\alpha$ 2,6Gal sequence commonly found on many glycoproteins.

The expression vector used to transfect the CHO cells is shown in FIG. 1. The vector was constructed as follows. ST3, a 1.6 kb cDNA encompassing the complete amino acid coding sequences for the $\beta$-galactoside $\alpha$ 2,6 sialyltransferase, was shotgun subcloned from an EcoRI digest of ST3 into M13mp19 as described by Weinstein, et al.(6). Although an internal EcoRI site was present, the two fragments were correctly oriented as determined by dideoxy sequencing(7). Site directed mutagenesis by the procedure of Zoller and Smith(8)

eliminated the internal EcoRI site using the primer GCCAAGGAGTTCCAGAT which binds to nucleotides 115–132. An A to G transition abolished the EcoRI recognition site, GGAATTC, but preserved the native amino acid coding sequence. The mutation in ST3 was confirmed by the dideoxy chain termination DNA sequencing method (7).

The nucleotide sequence of the sialyltransferase cDNA prior to mutagenesis at the EcoRI site is set forth in FIGS. 3a and 3b. Also shown is the complete amino acid sequence inferred from the nucleotide sequences. Peptide sequence overlaps (black boxes) include the NH₂-terminal sequence of the purified sialyltransferase (arrow). Stippled areas indicate residues that were not identified. Potential glycosylation sites with the sequence Asn-X-Thr/Ser are boxed. The proposed signal-anchor sequence is underscored with the cross-hatched box bordered at either end by open boxes highlighting charged lysine residues.

The altered cDNA was subcloned from M13mp19 into the EcoRI site of the polylinker of bluescript (bs-ST3) and subsequently into the EcoRI site of pECE (pECE-ST3) for expression of the sialyltransferase as shown in FIG. 1. In this vector the sialyltransferase cDNA is under the direction of SV-40 virus early promotor, allowing the sialyltransferase to be expressed in a wide variety of eukaryotic cell lines. The vector was obtained from William J. Rutter (University of California at San Francisco School of Medicine-Department of Biochemistry and Biophysics), and is described in Ellis, et al.(4)

CHO cells were transfected with pECE-ST3 according to the method of Graham and Van der Eb(9). Cells at 50% confluency were transfected with 20 ug supercoiled pECEST3 and 2 ug supercoiled pSV2neo per 100 mm dish. After 48 hours the cells were split 1:5 and replated in 75 cm² flasks with selection medium containing the antibiotic G418. After six weeks in selection medium, resistant cells were presumed to have the transfected DNA stably integrated in the genome, and the cells were then maintained in the absence of G418.

To select clonal cell lines expressing the sialyltransferase, advantage was taken of a newly described plant lectin, *Sambucus nigra* agglutinin (SNA), which recognizes the product of the sialyltransferase, NeuAcα 2,6Gal, with 50–100 fold higher avidity than the NeuAcα 2,3Gal sequence normally produced by the CHO cells.(10) Accordingly, cells producing the sialyltransferase were found to bind the fluorescent labeled lectin (FITC-SNA), but not the wild type cells. Following automated fluorescence activated cell sorting (FACS), clonal cell lines expressing the β-galactoside α 2,6 sialyltransferase were readily isolated and amplified.

Detailed analysis of one cell line showed that the β-galactoside α 2,6 sialyltransferase is expressed at equivalent levels to the endogenous β-galactoside α 2,3 sialyltransferase normally present in CHO cells. The result is that 20–25% of the total cell surface carbohydrate groups contain the NeuAcα 2,6Gal sequence instead of the NeuAcα 2,3Gal sequence. Thus, this cell line produced the mixture of sialic acid linkages found on many naturally produced glycoproteins, rather than only the NeuAcα 2,3Gal sequence produced by wild type CHO cells. This invention is therefore useful in the expression of recombinant glycoproteins such as erythropoietin, where the natural mixture of sialic acid linkages differs from that of the recombinant glycoprotein produced in CHO cells.

Figure 2:
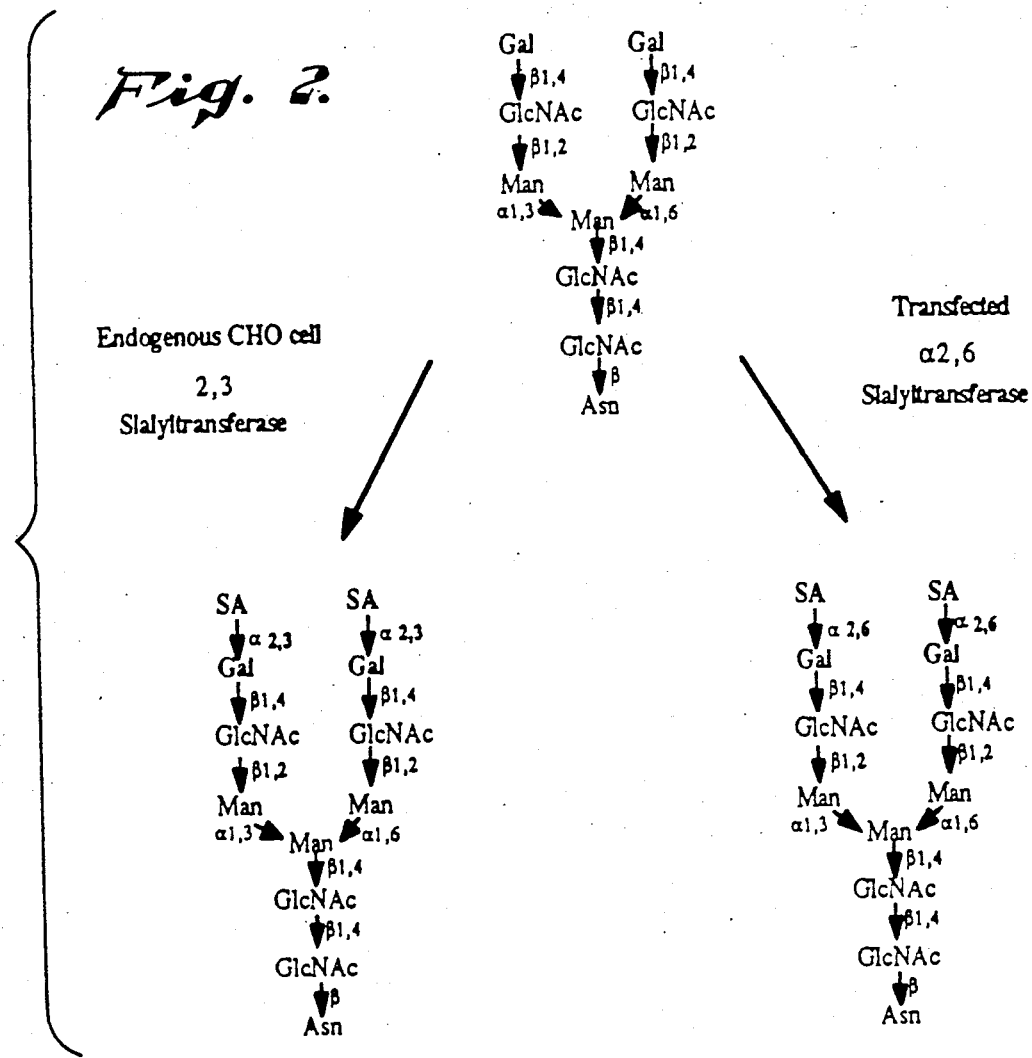
FIG. 2 is a diagrammatic representation outlining the mechanism by which applicant's process controls carbohydrate structure during glycosylation within CHO cells.

A comparison of the carbohydrate structures which result from addition of terminal sialyl acid groups in endogenous CHO cells and CHO cells transfected with the cDNA clone expressing the α 2,6 sialyltransferase is set forth in FIG. 2. In FIG. 2, GlcNAc=N-acetylglucosamine; Gal=galactose; Man=mannose; SA=sialic acid (N-acetyl neuraminic acid); and Asn=asparagine. As can be seen, the terminal SA groups in the endogenous CHO cells are only attached by α 2,3 linkages. However, the CHO cells which are modified in accordance with the present invention also produces α 2,6 terminal SA linkages.

The ratio of the NeuAcα 2,6Gal and NeuAc alpha 2,3Gal linkages can now be controlled by controlling the level of expression of the β-galactoside α 2,6 sialyltransferase. To this end an expression vector has been constructed placing the sialyltransferase under the control of the metallothionein promotor in a plasmid (pMT010/A+) containing the DHFR gene.(11) When transfected into cells, this vector allows a twofold control on the level of expression. The first is by induction of the metallothionein promotor with metal ions, and the second by amplification of the gene by selection with methotrexate. Such vectors will allow amplification of expression 100 fold over that obtained in the transfected cell lines examined to date.(11) Thus, a simple alteration of the procedure described above, will allow additional control over the terminal sialic acid linkages of CHO cells.

The general applicability of the procedure of the present invention is limited only by the availability of cDNA's coding for glycosyltransferases making terminal structures not normally found on the target cells, and the availability of an appropriate lectin or carbohydrate specific antibody capable of recognizing the newly expressed carbohydrate structure on the surface of the transfected cells. Numerous specific carbohydrate lectins and monoclonal antibodies suitable for this purpose have been reported and are available.(12,13)

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

BIBLIOGRAPHY (1) Takeuchi, M., et al. (1988) J. Biol. Chem 263, 3657–3663.
(2) Kagawa, Y., et al. (1988) J. Biol. Chem. 263, 17508–17515.
(3) Stanley, P. (1987) Meth. Enzymol. 138, 443–470.
(4) Ellis, L., et al. (1986) Cell 45, 721–732.
(5) Beyer, T., et al. (1981) Advances in Enzymol. 52, 24–175.
(6) Weinstein, et al., (1987) J. Biol. Chem. 17735–17743.
(7) Sanger, F. (1977) Proc. Nat. Acad. Sci. USA 74, 5463–5467.
(8) Zoller, M.J. and Smith, M. (1984) DNA 3, 479–488.
(9) Graham, F.L. and Van der Eb, A.J. (1973) Virol. 52, 456–467.
(10) Shibuya, N. (1987) J. Biol. Chem. 262, 1596–1601.
(11) Choo, K.H. et al. (1986) DNA 5, 529–537.
(12) Product catalogs of Sigma Chemical Co. and E.Y. Labs, San Mateo, Calif.

(13) Hakomori, S. (1984) In "Monoclonal antibodies and functional cell lines" (R.H. Kennett, K.B. Bechtol and T.J. McKearn) Plenum Pub. Corp. New York, pp. 67-100.

What is claimed is:

1. A process for altering the glycosylation of a protein produced by a eukaryotic cell, said process comprising the steps of:
   introducing into said eukaryotic cell at least one gene which is capable of expressing at least one enzyme which is selected from the group consisting of glycosyltransferase, fucosyltransferases, galactosyltransferases, β-acetylgalactosaminyltransferases, N-acetylglycosaminyltransferases and sulfotransferases; and
   expressing a sufficient amount of at least one of said enzymes in said eukaryotic cell to thereby alter the glycosylation of said protein in said eukaryotic cell.

2. A process according to claim 1 wherein said cell is selected from the group consisting of Chinese hamster ovary cells, mouse L cells, mouse A9 cells, baby hamster kidney cells, C127 cells and PC8 cells.

3. A process according to claim 1 wherein said gene is introduced into cell by transfection with a vector comprising cDNA which codes for said enzyme.

4. A process according to claim 3 wherein said cDNA has the nucleotide sequence set forth in FIGS. 3a and 3b of this specification.

5. A process according to claim 3 wherein said vector is selected from the group consisting of pECE, pMSG, pAV009/A+, pMT 101/A-.

6. A process according to claim 5 wherein said vector is pECE.

7. A process according to claim 6 wherein said cDNA has the nucleotide sequence set forth in FIGS. 3a and 3b of this specification.

8. A process according to claim 1 including the further step of recovering the protein for which glycosylation was altered.

9. A process for altering the glycosylation of a protein produced by a cell wherein attachment of the carbohydrate moiety to said protein during glycosylation is dependent upon at least one naturally occurring enzyme present in said cell, said process comprising the steps of:
   introducing into said cell at least one gene which is capable of expressing at least one supplemental enzyme selected from the group consisting of sialyltransferase, fucosyltransferase, galactosyltransferase, N-acetylgalactosaminyltransferase, N-acetylglucosaminyltransferase and sulfotransferase; and
   expressing a sufficient amount of at least one of said supplemental enzymes in said cell to produce a cell having both naturally occurring and supplemental enzymes wherein the presence of said supplemental enzyme alters the glycosylation of said protein.

10. A process according to claim 9 wherein said cell is selected from the group consisting of Chinese hamster ovary cells, mouse L cells, mouse A9 cells, baby hamster kidney cells, C127 cells and PC8 cells.

11. A process according to claim 10 wherein said cell is a Chinese Hamster ovary cell and said enzyme is β-galactoside α 2,6-sialyltransferase.

12. A process according to claim 9 wherein said gene is introduced into cell by transfection with a vector comprising cDNA which codes for said enzyme.

13. A process according to claim 12 wherein said cDNA has the nucleotide sequence set forth in FIGS. 3a and 3b of this specification.

14. A process according to claim 12 wherein said vector is selected from the group consisting of pECE, pMSG, pAV009/A+, pMT010/A+.

15. A vector for use in expressing a sialyltransferase in a host cell, said vector comprising cDNA having the nucleotide sequence set forth in FIGS. 3a and 3b of this specification.

16. A vector according to claim 15 wherein said cDNA is cloned in a pECE vector.

* * * * *